US012773122B2

(12) United States Patent
Vespasiani

(10) Patent No.: US 12,773,122 B2
(45) Date of Patent: Oct. 27, 2026

(54) POCKET EQUIPMENT FOR PERFORM BIOIMPEDENTIOMETRIES AT HOME

(71) Applicant: METEDA S.R.L., Rome (IT)

(72) Inventor: Marco Vespasiani, Rome (IT)

(73) Assignee: METEDA S.R.L., Rome (IT)

( * ) Notice: Subject to any disclaimer, the term of this patent is extended or adjusted under 35 U.S.C. 154(b) by 275 days.

(21) Appl. No.: 18/549,710

(22) PCT Filed: Mar. 10, 2022

(86) PCT No.: PCT/IB2022/052171

§ 371 (c)(1),
(2) Date: Sep. 8, 2023

(87) PCT Pub. No.: WO2022/190038

PCT Pub. Date: Sep. 15, 2022

(65) Prior Publication Data

US 2024/0180442 A1 Jun. 6, 2024

(30) Foreign Application Priority Data

Mar. 12, 2021 (IT) ........................ 202021000001286

(51) Int. Cl.
*A61B 5/0537* (2021.01)
*A61B 5/00* (2006.01)

(52) U.S. Cl.
CPC .... *A61B 5/0537* (2013.01); *A61B 2560/0214* (2013.01); *A61B 2560/0431* (2013.01);
(Continued)

(58) Field of Classification Search
CPC .......... A61B 5/0537; A61B 2560/0214; A61B 2560/0431; A61B 2560/045;
(Continued)

(56) References Cited

U.S. PATENT DOCUMENTS

2012/0110228 A1* 5/2012 Vlach .................. A61B 5/0006 710/313
2012/0183259 A1 7/2012 Schwandt et al.
2015/0272466 A1* 10/2015 Laakkonen ............ A61B 5/274 600/509

FOREIGN PATENT DOCUMENTS

EP 3 387 987 A1 10/2018
GB 2 385 137 A 8/2003
IT UA20 163 646 A1 11/2017

OTHER PUBLICATIONS

Total Phase 2020 (Year: 2020).*
(Continued)

*Primary Examiner* — Justin Xu
(74) *Attorney, Agent, or Firm* — Troutman Pepper Locke LLP

(57) ABSTRACT

A pocket-sized apparatus for carrying out bioimpedance measurements at home includes: a closed box-like casing (1), which contains a printed circuit board (2), an micro-processor integrated control unit (3), and an integrated circuit bioimpedance meter device (4), interfaced to the integrated control unit (3).
A plurality of electrodes (11), arranged outside said casing (1) carry electrical signals to/from the bioimpedance meter device (4); a multi-pin connector (7), secured to the printed circuit board (2) and electrically connected to the control unit (3) and the bioimpedance meter device (4), can also be connected to a dedicated charging cable.
Status indicator means (8) are also provided, which are driven by the control unit (3) and visible from outside the casing (1).
An application for a portable personal terminal (20) connects (10) with the control unit (3) and acquires data produced by the bioimpedance meter device (4) for display.

7 Claims, 3 Drawing Sheets

(52) U.S. Cl.
CPC ..... *A61B 2560/045* (2013.01); *A61B 2562/04* (2013.01); *A61B 2562/166* (2013.01); *A61B 2562/227* (2013.01)

(58) Field of Classification Search
CPC .......... A61B 2562/04; A61B 2562/166; A61B 2562/227; A61B 2562/226; A61B 5/4872; A61B 5/4875
See application file for complete search history.

(56) References Cited

OTHER PUBLICATIONS

Altium 2020 (Year: 2020).*
Agcayazi Talha et al., "Wearable infant hydration monitor," 2016 IEEE Virtual Conference on Applications of Commercial Sensors (VCACS), IEEE, Jun. 15, 2016, pp. 1-10, 10 pages.
International Search Report (ISR) for International Application No. PCT/IB2022/052171, mailed Aug. 30, 2022, 4 pages.
Written Opiion of the International Searching Authority (ISA/EP), for International Application No. PCT/IB2022/052171, mailed Aug. 30, 2022, 8 pages.

* cited by examiner

POCKET EQUIPMENT FOR PERFORM BIOIMPEDENTIOMETRIES AT HOME

TECHNICAL FIELD

The present innovation relates to the field of electromedical instruments intended for carrying out diagnostic examinations, in particular in the field of so-called preventive medicine, on patients with problems of balance in their body composition and metabolism, or also on healthy and balanced people wishing to keep their physical state under continuous control.

In particular, the present invention relates to a portable, automatic and extremely inexpensive apparatus, that is simple to use for performing bioimpedance analysis, that is for determining the the fat-to-lean mass ratio, hydration (percentage of body water) and in general for obtaining information relating to the metabolism of the person being examined by measuring impedance values detected in predetermined positions of the body.

BACKGROUND ART

Professional equipment is known to those skilled in the art for carrying out the measurements described above, and are technically called impedance meters, which basically consist of a central computer unit comprising a high-frequency voltage generator (usually around 50 KHz), connected to two or more electric current injector electrodes. The electrodes are to be positioned on the person's body and intended to apply a high-frequency current produced by the generator to the person, with very weak current values and without any dangerous effects on health. A voltage-measuring device is connected to one or more additional receiving electrodes, to be applied to the person's body in predetermined positions and dependent on the position of the injector electrodes, in order to detect the electrical voltage induced by the injector electrodes in the chosen detection zone and thus to enable the impedance of the person's body, or of the chosen zone of the body, to be assessed; a computerized control unit is connected to the voltage generator and the measuring device and intended to control activation of the former according to predefined sequences and frequencies, and to simultaneously detect the measurements made by the latter. A program for managing the operation of the impedance meter provides for both the performance of the operations described above and the display of data relating to the resistance and reactance values measured, and also makes this data available on suitable communication channels. Specialized software, generally residing on platforms external to the bioimpedance meter, subsequently implements well-known algorithms for processing and analyzing the measurements taken and calculating the person's hydration values, the person's fat-to-lean mass ratio, as well as for extrapolating further information relating to his metabolism from the measurements. One or more graphic displays allow the display of operating instructions for the equipment, measurement, and processing results in numerical or graphical form, and any warning, error or information messages. Operating commands can be given by the operator to the equipment by means of dedicated keys or alphanumeric keypads, either physical or virtual (in the form of touch screens, or touch-operated displays).

The injector electrodes are applied to the person under test, who is appropriately lying on a couch, usually on the hands and/or feet. Receiving electrodes are then applied, and an alternating current of constant absolute value is injected. The corresponding voltage value is detected by the receiving electrodes, acquired by the control unit and processed to obtain the desired impedance values. This operation is usually performed following well-identified operating protocols in order to obtain more precise and repeatable results. The measured value of body impedance derives directly from the mass of water present in the body and its dislocation in the various parts of the body at the time of measurement (lungs, lower limbs, etc.), which are influenced by the upright posture and only stabilize following the assumption of a prolonged declivity posture.

The methodologies used to perform the bioimpedance examinations described above are basically known and do not directly relate to innovation and will therefore not be discussed any further in the following.

Technical Problem

Impedance meters (or 'bioimpedance meters') of the type described above are conceived, designed, and constructed for professional use. These are complex equipment, both to make and to use, and are rather expensive and bulky. The person on whom the test is performed must be placed in a supine position and may not actively participate in the performance of the test. In addition, the person must necessarily go to the professional center where the equipment is installed. This usually implies a high cost of the operation and considerable loss of time, especially when the person has to perform impedance tests regularly, in order to monitor his or her physical condition and metabolism.

Other devices are also known that performs impedance tests more simply and automatically. Such devices consist of common platform scales that, in addition to having a device for measuring body weight, have an injector and a receiver electrode on opposite sides of the platform. The person to be tested stands barefoot and the equipment measures weight and simultaneously takes an impedance measurement, which is then processed in an internal control unit to provide a rough assessment of the person's hydration and fat-to-lean mass ratio.

The test carried out with this type of impedance meter, which requires orthostatism, is inherently inaccurate and essentially useless for the needs of precise and repeatable evaluations related to pathologies or metabolic dysfunctions.

OBJECTS OF THE INVENTION

The object of the present innovation is to provide an apparatus for performing impedance measurement tests on a person, and to provide consequent assessments on the body water balance, on the fat-to-lean mass ratio and in general on the metabolism of the same person, which has minimal dimensions such that it can be carried in a pocket or worn for long periods of time, that it is easy to use so that it can be readily used safely and with reliable results by the person, and that requires a cost low enough to make it affordable for anyone interested in keeping a constant check on their physical condition.

A further object of the innovation is to provide a piece of equipment that can be easily used to perform periodic, continuous and/or long-term bioimpedance measure evaluations. These operational modes are particularly significant for an overall assessment of the person's metabolic situation over the course of a day. The results obtained by continuous monitoring are potentially very useful, especially in persons with labile cardiac compensation and nephropathic patients.

SUMMARY OF THE INVENTION

The above objects, and others, are entirely achieved by a pocket-size apparatus for performing bioimpedance measurements at home, including: a closed box-shaped housing, which contains a printed circuit board, an integrated microprocessor control unit, and an integrated circuit bioimpedance meter device interfaced to the integrated control unit.

A plurality of electrodes, arranged outside said casing, carry electrical signals to/from the bioimpedance meter device; a multi-pin connector, secured to the printed circuit board and electrically connected to the control unit and the bioimpedance meter device, can also be connected to a dedicated charging cable.

Status indicator means are also provided, which are driven by the control unit and visible from outside the casing.

The apparatus is provided with control means, data processing means and result displaying means, comprising a dedicated application for a portable personal terminal, which are resident on said portable personal terminal and designed to connect with the control unit and intended to acquire data produced by the bioimpedance meter device and to display the results on a display of the portable personal terminal.

BRIEF DESCRIPTION OF THE DRAWINGS

The characteristics of the invention not emerging from what above will be made apparent in the following description, to be taken with reference to the enclosed drawings, in which.

DETAILED DESCRIPTION OF EMBODIMENTS

Figure 1:
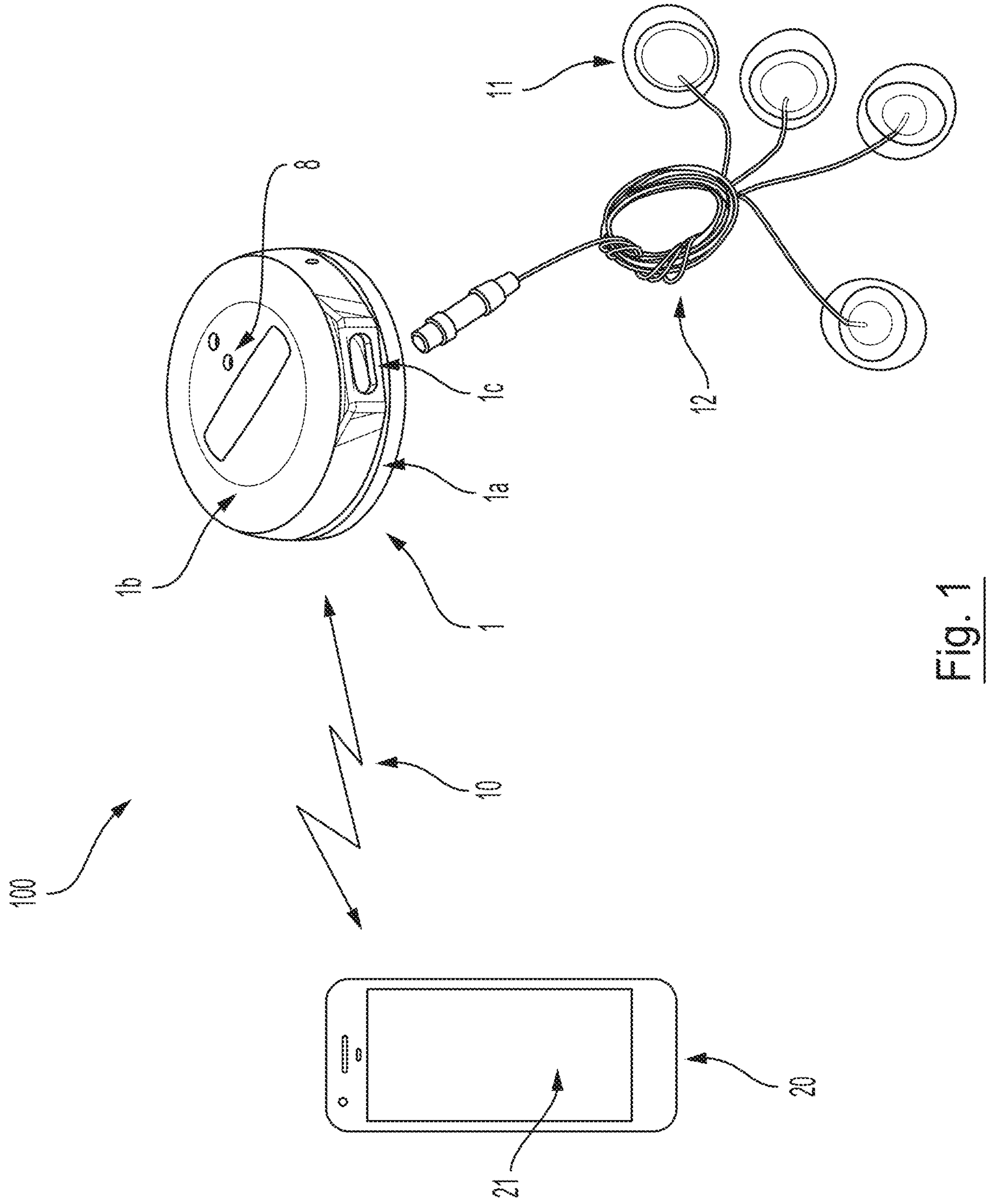
FIG. 1 schematically illustrates a preferred configuration of the pocket-sized apparatus for carrying out bioimpedance measurements made according to the innovation.
Figure 2:
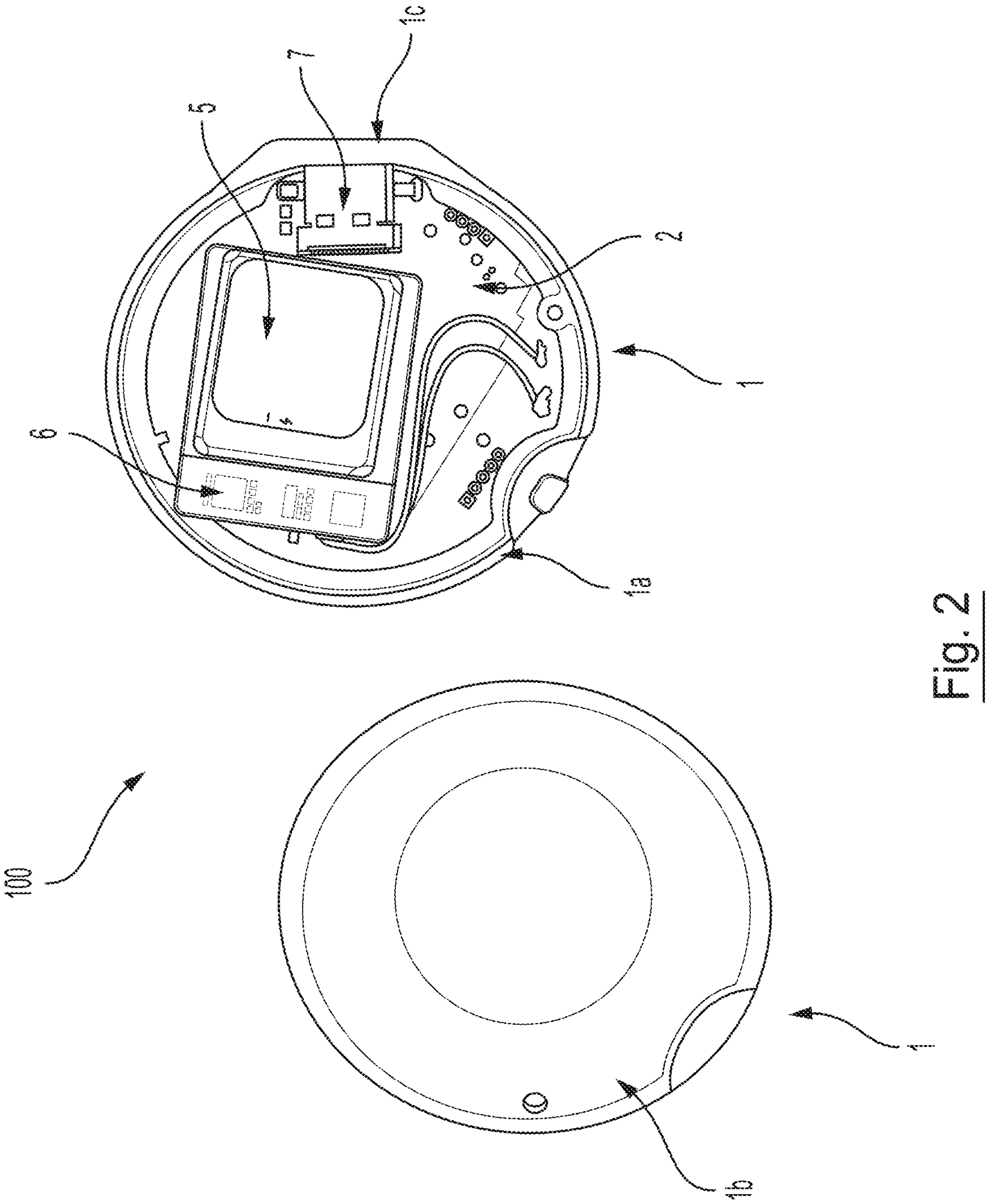
FIG. 2 illustrates a view of the apparatus in FIG. 1 with the casing open.
Figure 3:
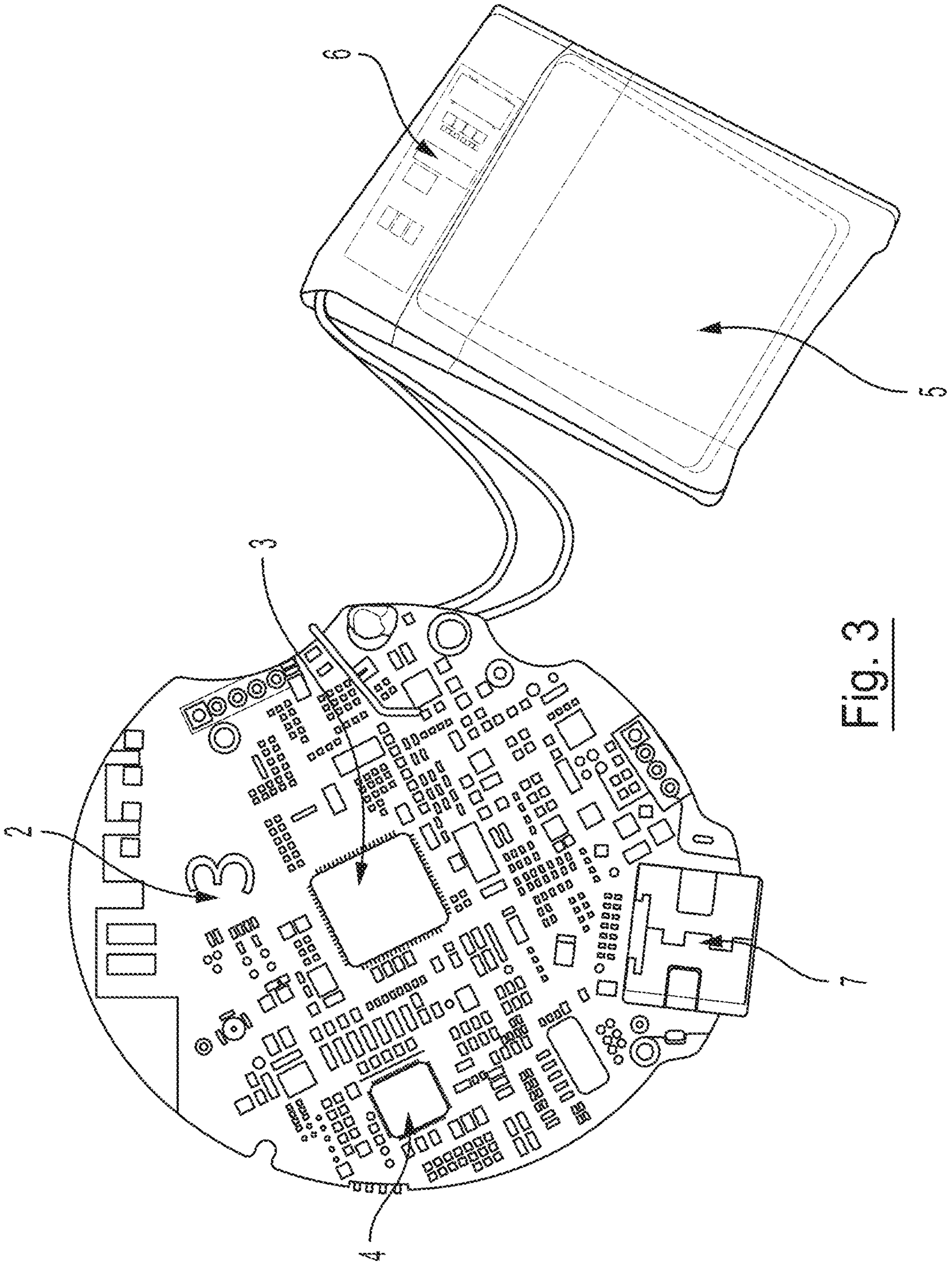
FIG. 3 illustrates a view of the electronics and power supply of the apparatus in FIG. 1.

With reference to the above figures, 100 indicates an apparatus for carrying out bioimpedance tests on the body of a person realized according to an embodiment of the innovation.

In particular, the apparatus 100 comprises a small rounded closed box-shaped casing 1, in particular with a diameter of about 4-5 centimeters, intended to house the internal components of the apparatus, which will be described in greater detail below.

The casing 1, in the embodiment shown herein, has a discoidal shell shape, and is realized with two half-shells 1*a*, 1*b* capable of being closed one on top of the other, fixed by interlocking means or screws. An opening 1*c* is provided to allow the internal components to physically connect with the outside.

The apparatus 100 further comprises a printed circuit board 2, that is so shaped as to be housed within the casing 1 and intended to contain substantially all of the electronic components of the apparatus.

These components comprise a microprocessor integrated control unit 3, of commercial type, within which a software program is contained and executed for managing the operations related to the performance of a bioimpedance measurement test and for communicating with the external environment. The software program is designed and realized according to the dictates of the programming technique for a microprocessor computer, and performs functions that do not directly pertain to the invention, so its structure will not be further described. The circuitry of the control unit 3 and/or of the board 2 also comprises wire and radio-wave communication means, as well as a plurality of input/output lines, all of a strictly standard type, intended to allow the aforementioned apparatus 1 to communicate with the external environment and with the internal devices of the apparatus 1 itself.

In particular, the wired communication means may be realized according to standards known as USB, and the radio-wave communication means may comprise a "wireless" communication line 10 (FIG. 1) realized according to standards known as Bluetooth® wireless communication protocol, Wi-Fi or another commercial standard, for connecting the casing 1 to a portable personal terminal 20, such as a smartphone or tablet PC.

The printed circuit board 2 also includes a single integrated circuit bioimpedance meter device 4, a device that has only recently become commercially available and affordable. This device is interfaced with the aforesaid control unit 3 by means of one or more input/output lines and provides means within itself for producing and injecting a constant electric current at a high frequency, typically about 50 KHz, and means for detecting an electric voltage, or potential difference, depending on the electric impedance (resistance+reactance) of the body crossed by the aforesaid constant current.

For this reason, the bioimpedance meter device 4 includes lines for operating a plurality of electrodes 11; more precisely, it includes injector electrodes, intended to inject the aforementioned high frequency constant current, and receiver electrodes, intended to detect the electrical voltage resulting from the injected current flow.

By the above-mentioned means, the device 4 is capable of autonomously performing the sequence of operations necessary to perform impedance measurement tests on a person and to make the raw results available to the above-mentioned control unit 3. Also in this case, it is not considered useful to go into the methodology and details of performing the test, as it is known and not strictly relevant to the invention.

The aforementioned electrodes 11 are connected to a single signal cable 12 intended to establish the electrical connection with the bioimpedance meter device 4, so as to carry electrical signals to/from the device itself. The electrodes may be, for example, four in number, in order to allow bioimpedance measurement tests to be carried out in a manner entirely similar to professional devices, and with results in measurement accuracy comparable with them.

In this regard, the apparatus 100 comprises a multi-pin connector 7 which, for reasons of limiting the size of the apparatus, is preferably the only connector provided. The connector 7 is conveniently connected to the control unit 3 and the bioimpedance meter device 4. It also establishes a connection to a charging circuit 6 of a rechargeable storage battery 5, the latter intended to supply power to the printed circuit board 2 and the devices therein.

In this way a single connector 7 can be used to alternatively connect the electrodes 11 to the apparatus 1, when carrying out the impedance measurement tests by means of the signal cable 12, in turn a suitable charging cable to supply energy to the apparatus 1 itself or, possibly, a USB-type data cable, used to establish a data connection between the control unit 3 and the aforementioned portable personal terminal 20.

The signal cable 12 and the charging cable can preferably be completely independent or, if considered more convenient, be wrapped within a single sheath and use the same connector to connect to the multi-pin connector 7.

In order to recognize the type of connection currently established by the multi-pin connector 7, the apparatus 1 may provide suitable sensor means, of a known type, connected to the control unit 3 and to the same connector 7, to recognize and alternatively signal the presence of the signal cable (12) or of the charging cable.

In the printed circuit board 2, there are also provided status indicator means 8, driven by the aforementioned control unit 3 and visible from the outside of the housing, by transparency or through suitable openings therein.

The status indicator means 8 are provided for signalling the current status of the apparatus 100 to the user and are realized with one or more LEDs, also multi-colored, for reasons of constructive and operational simplicity, as well as for space and cost containment.

In order to provide the user with a clear, complete, and interactive interface in relation to the operations for activating the apparatus 100, reading the results and interpreting and storing them, means for processing the data and displaying the results are also provided, consisting of an application resident and operating in the above-mentioned personal interactive terminal 20. The application is programmed to interface with the user via a display 21 of the terminal 20 and with the control unit 3 via the communication line 10, through the means already provided for this purpose in the aforementioned terminal 20 itself.

The operation of the apparatus 1 can be carried out by a non-professional user readily and in a very simple and automated manner, or in any case guided via the application previously installed, for example on the smartphone 20 of the same. It is intended that, of course, the apparatus 1 can also be conveniently used in professional settings, by healthcare personnel wishing to take advantage of the advantageous features and applications resulting from the innovation, which will be further highlighted below.

The use of the apparatus 1 for carrying out a bioimpedance measurement test involves first of all recharging the battery 5 by means of the recharging cable and a suitable source of electric power.

The particular compactness, the simplicity of use and the operational autonomy of the apparatus 1 described above allow it to be used in at least two operating modes: a single test mode and a continuous test mode, or in any case periodic over long running times (bioimpedance measurement "Holter" mode). The latter mode, in particular, usually involves performing a predefined number of bioimpedance measurement tests over a period of 24 hours, or more, and storing them to allow for further specialist evaluations. The "Holter" mode is particularly significant for obtaining a global evaluation of the evolution of the person's metabolic situation, and on the presence of possible dysfunctions of the same in normal life conditions, certainly not reproducible during a conventional bioimpedance measurement test session.

In the following, the single-test operating mode will be described, as the Holter mode is directly and immediately derived from the former. With sufficient stored energy, the user pulls out the charging cable and inserts the signal cable 12 into the multi-pin connector 7. Subsequently (or even previously), guided by the application installed on his smartphone 20, the person places the injector and receiver electrodes at predefined positions on his body, after which he sends a command to activate the test.

The application sends the commands received to the control unit 3, which in turn commands the bioimpedance meter device 4 to perform a test, the data of which are then transmitted to the control unit 3 and from the latter, via the wireless communication line 10, back to the application, which processes the results, stores them and shows them on the display 21 of the smartphone 20. Processing of the results can also be carried out by means of remote programs, resident in a 'cloud' service and accessible from the application by means of appropriate connections made by the smartphone 20.

As mentioned above, an advantageous operational alternative, which is only possible with the apparatus 100 of the innovation, consists in activating a "Holter" type operating mode, i.e. a continuous monitoring of the user's bioimpedance parameters for a predetermined period of time.

In this case, the user, after activating the relevant function in the dedicated application, setting a given run time or a given number of operating cycles, keeps the apparatus 100 with him/her, e.g., in a pocket or attached to the skin in a convenient area of his/her body. Then the person resumes his normal life actions, taking care to keep the smartphone 20 with him or in any case within operating range of the communication line 10 being used.

The application then autonomously carries out a series of periodic cycles of bioimpedance measurement tests and stores the results. At the end of the set limit, the user can view the results of the tests performed, either singly or following their aggregation and graphical or statistical processing, and possibly send them to his specialist for professional evaluation.

It is understood that what is described above has only an illustrative and not limiting aim. Therefore, possible modifications and variations of the innovation are considered to be within the protective scope granted to this technical solution as described above and claimed below.

The invention claimed is:

1. Apparatus, comprising:

a casing for carrying out bioimpedance measurements;

a printed circuit board, contained within said casing;

a microprocessor integrated control unit, suitable for receiving and executing a management program of said apparatus, the apparatus further comprising communication means for data exchange with a personal terminal device (20);

a bioimpedance integrated circuit meter device, interfaced to said integrated control unit, capable of autonomously performing impedance measurement test functions on a person and making available the raw results thereof;

a plurality of electrodes, arranged outside said casing and connected to a single signal cable for carrying electrical signals from/to said bioimpedance meter device;

a rechargeable storage battery, provided with a recharging circuit for supplying power to said printed circuit board;

a multi-pin connector, secured to said printed circuit board and electrically connected to said control unit and to said bioimpedance meter device, configured to alternatively receive said signal cable and a dedicated recharging cable, said multi-pin connector establishing, by means of said signal cable, connections between said electrodes and said bioimpedance meter device, and establishing, by means of said dedicated recharging cable, connections for said recharging circuit;

status indicator means, driven by said control unit and visible from the outside of said casing, for indicating a status of said apparatus; and wherein said personal terminal device includes control means, data processing means and result displaying means, comprising at least one dedicated application for connecting with said control unit via said data exchange, for acquiring data produced by said bio-impedance meter device, and for displaying results on a display of said personal terminal device.

2. The apparatus according to claim 1, wherein said dedicated application comprises instructions for activating said bioimpedance meter device, for acquiring said data and for processing and storing the results, either in a single cycle or according to multiple cycles periodically repeated for predetermined times or number of cycles, for performing a bioimpedance Holter-measurement.

3. The apparatus according to claim 1, wherein said communication means include communication via radio waves, operating using a standard protocol.

4. The apparatus according to claim 1, wherein said plurality of electrodes are four in number, and two of said plurality of electrodes are injector electrodes and two are receiver electrodes.

5. The apparatus according to claim 1, wherein said casing has a shell shape, and is made with two half-shells capable of closing on each other.

6. The apparatus according to claim 1, wherein said casing has a discoidal shape.

7. The apparatus according to claim 1, wherein said multi-pin connector is made according to a Universal Serial Bus (USB) standard.

* * * * *